United States Patent [19]

Kühle et al.

[11] Patent Number: 4,645,776

[45] Date of Patent: Feb. 24, 1987

[54] N-(DICHLOROFLUOROMETHYLTHIO)-3,4-DIMETHYLMALEIMIDE AND ITS USE AS A FUNGICIDE

[75] Inventors: Engelbert Kühle, Bergisch-Gladbach; Wilfried Paüliis; Hermann Genth, both of Krefeld, all of Fed. Rep. of Germany

[73] Assignee: Bayer Aktiengesellschaft, Leverkusen, Fed. Rep. of Germany

[21] Appl. No.: 721,341

[22] Filed: Apr. 9, 1985

[30] Foreign Application Priority Data

Apr. 26, 1984 [DE] Fed. Rep. of Germany ....... 3415532

[51] Int. Cl.$^4$ ..................... C07D 207/448; B27K 3/38
[52] U.S. Cl. .................... 514/425; 548/542; 548/548; 71/67; 106/18.22
[58] Field of Search ................. 548/542, 548; 514/425

[56] References Cited

U.S. PATENT DOCUMENTS

| | | | |
|---|---|---|---|
| 2,553,771 | 5/1952 | Kittleson | 514/425 |
| 3,036,088 | 5/1962 | Harris | 548/542 |
| 3,249,620 | 5/1966 | Kuhle et al. | 548/542 |
| 3,499,030 | 3/1970 | Kuhle et al. | 260/551 |

FOREIGN PATENT DOCUMENTS

| | | | |
|---|---|---|---|
| 689434 | 6/1964 | Canada | 548/542 |
| 0045907 | 2/1982 | European Pat. Off. | 548/548 |
| 0111452 | 6/1984 | European Pat. Off. | |
| 3203057 | 8/1983 | Fed. Rep. of Germany | |
| 0641161 | 2/1984 | Switzerland | 548/548 |
| 927834 | 6/1963 | United Kingdom | |

Primary Examiner—Glennon H. Hollrah
Assistant Examiner—D. B. Springer
Attorney, Agent, or Firm—Sprung Horn Kramer & Woods

[57] ABSTRACT

The new compound N-(dichlorofluoromethylthio)-3,4-dimethylmaleimide can be prepared by reacting 3,4-dimethylmaleimide with dichlorofluoromethanesulphenyl chloride in the presence of an acid-binding agent. N-(dichlorofluoromethylthio)-3,4-dimethylmaleimide is an active compound in microbicidal agents.

6 Claims, No Drawings

N-(DICHLOROFLUOROMETHYLTHIO)-3,4-DIMETHYLMALEIMIDE AND ITS USE AS A FUNGICIDE

The present invention relates to the new compound N-(dichlorofluoromethylthio)-3,4-dimethylmaleimide, a process for its preparation and its use as a microbicidal agent.

The use of N-(trihalogenomethylthio) compounds for preserving industrial materials from microbial degradation is known (U.S. Pat. No. 2,563,770, Journ. Agr. Food Chem. 14, 365 (1966), and Fette, Seifen, Anstrichmittel 68, 272 (1966)). However, they are not always satisfactory, since, in particular, they have a poor solubility in some paints and impregnating agents.

The new compound N-(dichlorofluoromethylthio)-3,4-dimethylmaleimide has been found.

The new compound N-(dichlorofluoromethylthio)-3,4-dimethylmaleimide has outstanding microbicidal properties and exhibits a good solubility, in particular in paints and impregnating agents.

A process has also been found for the preparation of the new compound N-(dichlorofluoromethylthio)-3,4-dimethylmaleimide, which is characterised in that 3,4-dimethylmaleimide is reacted with dichlorofluoromethanesulphenyl chloride in the presence of an acid-binding agent.

The process according to the invention can be illustrated by the following equation:

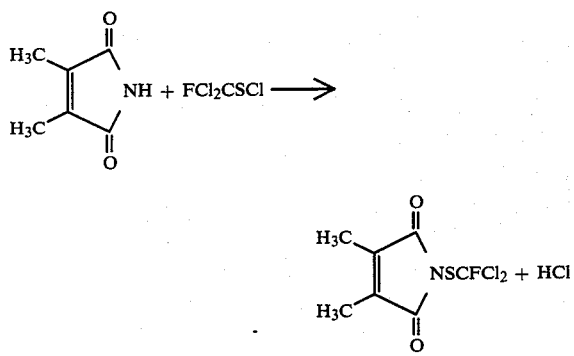

3,4-Dimethylmaleimide is known from Beilsteins Handbuch der organischen Chemie (Beilstein's Handbook of organic Chemistry), Volume 21, page 412.

Dichlorofluoromethanesulphenyl chloride is described in Angew. Chem. 76, 807 (1964).

Acid-binding agents for the process according to the invention can be, for example, sodium hydroxide, sodium carbonate, triethylamine or pyridine.

Solvents for the process according to the invention can be, for example, hydrocarbons, such as toluene, chlorohydrocarbons, such as chlorobenzene, ethers, such as dioxane, or water.

In general, 1 of 3,5-dimethylmaleimide is reacted with about 1 to 1.2 mols of dichlorofluoromethanesulphenylchloride in the presence of about 1 to 1.2 mols of an acid-binding agent.

The process according to the invention is in general carried out in the temperature range from 0° to 100° C., preferably from 20° to 50° C.

The process according to the invention is in general carried out under normal pressure. However, it is also possible to carry out the process under an increased or reduced pressure (for example in the pressure range from 0.5 to 1.5 bar).

The N-(dichlorofluoromethylthio)-3,4-dimethylmaleimide according to the invention can be used as an active compound for combating microorganisms, in particular for preserving industrial materials and in plant protection.

According to the invention, industrial materials are non-living materials which have been prepared for use in industry. Industrial materials which are to be preserved by the active compound according to the invention from microbial change or destruction can be, for example, adhesives, sizes, paper and card, textiles, leather, wood, paints and plastics, cooling lubricants and other materials which can be destroyed by microorganisms. In the context of the materials to be preserved, there may also be mentioned components of production installations for example cooling water circulations, which can be impaired by microorganisms. Adhesives, sizes, paper and card, leather, wood, paints and cooling circulations may be mentioned as preferred industrial materials in the context of the present invention. The preservation of devices and/or apparatuses made of wood may be mentioned in particular.

Examples of microorganisms which can cause degradation of or a change to the industrial materials are bacteria, fungi, yeasts, algae and slime organisms. The active compound according to the invention preferentially acts against moulds, fungi which discolour or destroy wood (Basidiomycetes) and slime organisms.

Microorganisms of the following genera may be mentioned as examples: Alternaria, such as *Alternaria tenuis*, Aspergillus, such as *Aspergillus niger*, Aureobasidium, such as *Aureobasidium pullulans*, Chaetomium, such as *Chaetomium globosum*, Coniophora, such as *Coniophora puteana*, Lentinus, such as *Lentinus tigrinus*, Penicillium, such as *Penicillium glaucum*, Polyporus, such as *Polyporus versicolor*, Sclerophoma, such as *Sclerophoma pityophila* and Staphylococcus, such as *Staphylococcus aureus*.

Depending on its field of use, the active compound according to the invention can be converted into the customary formulations, such as solutions, emulsions, suspensions, powders, pastes and granules.

These can be prepared in a manner which is known per se, for example by mixing the active compound with an extender, which consists of liquid solvent and/or solid carriers, if appropriate using surface-active agents, such as emulsifiers and/or dispersing agents, and, for example in the case of the use of aqueous extenders, organic solvents, such as alcohols, can also be used as auxiliaries, if appropriate.

Organic solvents for the active compound according to the invention can be, for example, alcohols, such as lower aliphatic alcohols, preferably ethanol or isopropanol, or benzyl alcohol, ketones, preferably acetone or methyl ethyl ketone, liquid hydrocarbons, preferably benzine fractions, or chlorinated hydrocarbons, preferably 1,2-dichloroethane.

The microbicidal agents in general contain the active compound in an amount of 1 to 95%, preferably 10 to 75%.

The use concentrations of the active compound according to the invention depend on the nature and occurrence of the microorganisms to be combated and on the composition of the material to be preserved. The optimum amount for use can be determined by test series. In general, the use concentrations are in the range from 0.001 to 5% by weight, preferably from 0.05 to 1.0% by weight, based on the material to be preserved.

The active compound according to the invention can also be present in a mixture with other active compounds which are known per se. The following active compounds may be mentioned as examples: benzyl alcohol mono(poly)hemiformal, benzimidazolyl methylcarbamates, tetramethylthiuram disulphide, zinc salts of dialkylthiocarbamates, 2,4,5,6-tetrachloroisophthalonitrile, thiazolylbenzimidazole, mercaptobenzothiazole, trialkyl-tin compounds, methylenebisthiocyanate, 2-thiocyanatomethylthio-benzthiazole and phenol derivatives, such as 2-phenylphenol, (2,2'-dihydroxy-5,5'-dichloro)-diphenylmethane and 3-methyl-4-chlorophenol.

The active compound according to the invention is also suitable for use in plant protection agents. The good tolerance of the active compound by plants in the concentrations necessary for combating plant diseases permits treatment of above-ground parts of plants, of vegetative propagation stock and seed and of the soil.

PREPARATION EXAMPLE

EXAMPLE 1

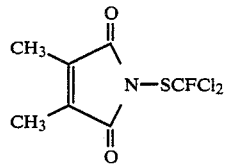

10.1 g (0.08 mole) of dimethylmaleimide are dissolved in 100 ml of toluene with the addition of 15 g (0.089 mole) of dichlorofluoromethanesulphenyl chloride. 9.4 g (0.093 mole) of triethylamine are added dropwise to this solution at room temperature and the temperature is allowed to rise to about 60° C. The reaction solution is washed with water, the toluene phase is dried, the solution is concentrated in vacuo and the residue is recrystallized from naphtha. Melting point: 47° to 49° C. Yield: 13.5 g.

USE EXAMPLES

Example 1

To demonstrate the activity against fungi, the minimum inhibitory concentrations (MIC) of N-(dichlorofluoromethylthio)-3,4-dimethylmaleimide are determined:

N-(Dichlorofluoromethylthio)-3,4-dimethylmaleimide is added in concentrations of 0.1 mg/l to 5,000 mg/l to an agar prepared from beerwort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which no growth at all of the species of microbe used takes place, and is given in the following table.

| MIC values in mg/l for the action of N—(dichlorofluoromethylthio)-3,4-dimethylmaleimide on fungi | |
|---|---|
| Alternaria tenuis | 0.75 |
| Aspergillus niger | 50 |

| -continued | |
|---|---|
| MIC values in mg/l for the action of N—(dichlorofluoromethylthio)-3,4-dimethylmaleimide on fungi | |
| Aureobasidium pullulans | 0.5 |
| Chaetomium globosum | 50 |
| Coniophora puteana | 0.75 |
| Lentinus tigrinus | 1.5 |
| Penicillium glaucum | 5 |
| Polyporus versicolor | 7.5 |
| Sclerophoma pityophila | 1 |
| Trichoderma viride | 100 |

Example 2

(Action against slime organisms)

N-(Dichlorofluoromethylthio)-3,4-dimethylmaleimide (dissolved in a little acetone) is used in concentrations of in each case 0.1 to 100 mg/l in Allens nutrient solution (Arch. Mikrobiol. 17, 34 to 53 (1952)), which contains, in 4 l of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam. Shortly beforehand, the nutrient solutions are infected with slime organisms (about $10^6$ germs/ml) which have been isolated from spinning water circulations used in the production of polyamide. Nutrient solutions which contain the minimum inhibitory concentration (MIC) or higher concentrations of active compound are still completely clear after culture at room temperature for 3 weeks, that is to say the marked increase in microbes and slime formation noticeable after 3 to 4 days in nutrient solutions containing no active compound are absent.

The following MIC can be determined in this manner for N-(dichlorofluoromethylthio)-3,4-dimethylmaleimide: 7.5 mg/l.

Example 3

Test of N-(dichlorofluoromethylthio)-3,4-dimethylmaleimide as a paint fungicide

The testing is carried out in accordance with the method in Report 219 of the Defense Standards Laboratories Maribyrnong/Australia, as follows: A smooth card is coated on both sides with the paint to be tested and dried at room temperature for 8 days. For ageing, part of the paint film is kept in running water of 24° C. for 24 hours, or aerated with fresh air of 40° to 60° C. for 8 days, or subjected to a dry Xenon test for 110 hours. 5×5 cm sections of the samples thus prepared are placed individually on a glucose nutrient medium in Petri dishes and contaminated with a spore suspension of the following fungi: Aspergillus niger, Aureobasidium pullulans, Alternaria tenuis, Penicillim citrinum, Stachybotrys atra, Paecilamyces varioti, Cladosporium herbarum, Aspergillus ustus and Aspergillus flavus.

The contaminated dishes are kept at 28° to 30° C. and 90 to 95% relative atmospheric humidity, and are evaluated after 3 weeks. Paint films are regarded as mould-resistant if the samples remain free from fungi after these tests.

A commercially available lacquer paint based on alkyd resin is tested for mould-resistance by the above-mentioned test method.

The following evaluation results after the test: Paint films of the lacquer paint containing 0.8% of N-(dichlorofluoromethylthio)-3,4-dimethylmaleimide, based on the weight of film, are mould-resistant, even if they have been exposed to the abovementioned ageing processes before microbiological testing.

What is claimed is:

1. N-(Dichlorofluoromethylthio)-3,4-dimethylmaleimide.

2. A fungicidal composition comprising a fungicidally effective amount of N-(dichlorofluoromethylthio)-3,4-dimethylmaleimide and a fungicidal agent compatible diluent.

3. A fungicidal composition according to claim 2 wherein said N-(dichlorofluoromethylthio)-3,4-dimethyl-maleimide is present in an amount of 1 to 95% by weight based upon the weight of said fungicidal composition.

4. A process for combating a fungi which comprises applying thereto or to its habitat a fungicidally effective amount of N-dichlorofluoromethylthio)-3,4-dimethylmaleimide.

5. A process according to claim 4, wherein said N-(dichlorofluoromethylthio)-3,4-dimethylmaleimide is applied to wood.

6. A process according to claim 4 wherein such N-(dichlorofluoromethylthio)-3,4-dimethylmaleimide is applied in an amount of 0.001 to 5% by weight based upon the wood.

* * * * *